United States Patent [19]

Seguin et al.

[11] Patent Number: 4,784,854

[45] Date of Patent: Nov. 15, 1988

[54] COSMETIC COMPOSITION OBTAINED FROM CELLULAR CULTURES OF CONJUNCTIVE TISSUE

[76] Inventors: Marie-Christine Seguin; Jean Gueyne, both of Perigord 1, 6 Lacets Saint-Leon, Monte-Carlo, Monaco

[21] Appl. No.: 891,679

[22] Filed: Jul. 29, 1986

[30] Foreign Application Priority Data

Aug. 1, 1985 [FR] France ................ 85 11766

[51] Int. Cl.$^4$ ............... A01N 63/02; A61K 35/12; A45D 44/00
[52] U.S. Cl. .................... 424/401; 424/95; 604/307; 401/88
[58] Field of Search .......... 132/1 R; 604/307; 424/95, 401

[56] References Cited

U.S. PATENT DOCUMENTS

| | | | |
|---|---|---|---|
| 2,296,207 | 9/1942 | Kittinger | 604/307 |
| 3,297,034 | 1/1967 | Peary | 604/307 X |
| 3,910,284 | 10/1975 | Orentreich | 132/1 X |
| 3,995,025 | 11/1976 | Aubert | 424/95 |
| 4,134,557 | 2/1982 | Chandrasekaran | 604/307 X |
| 4,304,866 | 12/1981 | Green et al. | 424/95 X |
| 4,670,257 | 6/1987 | Sagliar et al. | 424/95 |
| 4,675,009 | 6/1987 | Hymes et al. | 604/307 X |

Primary Examiner—Michael R. Lusignan
Attorney, Agent, or Firm—Ostrolenk, Faber, Gerb & Soffen

[57] ABSTRACT

Cosmetic composition for treatment of the skin, comprising conjuctive tissue cells, particularly fibroblasts, in a nutrient medium, in which growth of the cells can occur. Flat support having an adhesive coated periphery, carrying or containing this composition, covered with a film insoluble in water. Preparation of the composition by the culture of fibroblasts in a modified Eagle medium.

18 Claims, 1 Drawing Sheet

COSMETIC COMPOSITION OBTAINED FROM CELLULAR CULTURES OF CONJUNCTIVE TISSUE

The present invention relates to a new cosmetic composition and its preparation, the composition being intended principally for improving the appearance and quality of the skin. The invention also comprises articles or devices for manufacturing this composition and/or for application of it to the skin.

Improvement in the quality of the skin constitutes one of the main objectives in cosmetology. It is in fact often necessary to stimulate natural regeneration of the skin and, outside, its colouration, moisturisation, nutrition or protection against the sun's rays or the wind. Also, there are a large number of creams, lotions and milks based on various natural or synthetic products, employed with a view to the stimulation of the normal processes, in order to give skin, more or less damaged or aged, the desirable suppleness, tone and appearance. These, ranging from various vegetable and animal fatty materials, for example, sweet almond or palm oil and horsehair or mink fur grease, some of which have been used for centuries, to compositions based on extracts of rubber, collagen, placenta, vegetables and vitamins. A large number of products have been used experimentally with widely varying results. As regards truly restoring strength, suppleness and lustre to skin, the compositions employed up to the present have been unsatisfactory.

The present invention provides a substantial improvement in this field. It modifies the poor state and appearance of the skin by means of a cytological composition, the purpose of which is to transmit to the skin cellular vectors, in a growth environment; these vectors exert a stimulatory action on tissue regeneration or even a repair effect. Thus, according to the invention, it is not a question, as is generally the case in the prior art, of applying foreign materials to the skin, but of inducing there natural phenomena of growth by means of specific factors of the skin itself.

The new composition according to the invention comprises a culture of cells in an appropriate growth medium suitable for cosmetic treatments; the cells are preferably those of a conjunctive tissue, in particular fibroblasts of conjunctive origin. While the cells of the culture can be human, unspecified animal or even vegetable, living or dead, particularly favourable results are obtained with cultures of human fibroblasts and keratinocytes. It can be of interest to employ a culture of fibroblasts obtained from an explant of the corresponding cells, taken from the subject who is intended to receive the given cosmetic composition according to the invention.

The process of preparation of the composition according to the invention can be carried out by a cellular culture according to the following technique. Human fibroblasts are isolated from fragments of skin and are freed from subcutaneous fatty tissue. Fragments of about 1 mm$^3$ are placed in culture containers and are covered with 1 ml of DMEM medium (Eagle) associated with a 10% foetal calf serum, 2 mM of glutamine, 1 mM of sodium pyruvate, non-essential amino acids and 100 units/ml of penicillin-streptomycin. The cultures are incubated at 37° C. in a humid atmosphere comprising 95% air and 5% $CO_2$.

The fibroblasts grow from the explant; they can be harvested after two to three weeks. The cells are detached quantitatively from the culture container after 5 min of exposure to a trypsin solution and are recovered after centrifugation at 1700 r/mn. They are suspended in the culture medium and distributed in culture supports at an initial density of $1 \times 10^2$ to $1 \times 10^8$ cells.

The nutrient medium employed can be liquid, pasty, particulate or solid; for example, it can take the form of a physiological serum, distilled water, a gel with gelatin or some other gel-forming material, microspheres of treated glass, inert powder, for example a polymer, PVC micronised at 20 microns, polyester fibres, collagen film etc.

The cellular support in the new cosmetic composition can contain a very variable number of cells, for example $10^2$ to $10^8$ per ml and preferably about $10^4$ to $10^8$.

While the composition can be constituted by conjunctive tissue cells or other cells, taken from a given subject and suspended in a medium suitable for their culture, the preferred form of the invention is a culture in which growth of the initial cells has been multiplied by at least 10. Particularly effective compositions contain about 10 to 100 times the initial number of seed cells.

Fibroblasts and keratinocytes, the preferred cells for the composition according to the invention, can be taken from the skin at any part of the human, animal or vegetable body. In man, it is practical to take a very small quantity of skin of the earlobe or thigh, for example. Explants in culture supports are thus maintained at 37° C., until their number multiplies in the desired proportion, as already indicated above.

After this phase of growth and proliferation, whatever the cell concentration in the culture medium, if the cells are dead, the composition should be stored cold, preferably between 1° C. and 6° C. and most preferably at 4° C.; if they are live, the composition is stored at 37° C. or −80° C. If the culture support is liquid, the composition can be put up in closed tubes, flasks or ampoules, as is known for various pharmaceutical and cosmetic products; however, according to two important embodiments, the new cosmetic composition is stored in a special device which, while ensuring excellent storage, facilitates application of the composition to the skin of the user. These devices constitutute an article which is also part of the invention.

According to a first aspect of the invention, the article comprises at least three superposed layers, the nutrient support and the cells being in this case in the form of a plate of very low thickness or a sterile film former, for example a film of vegetable origin, flax or cotton fibres, biologically nonstructured sheet-like or animal alginic acid gel, gelatin film, or structured; collagen; collagenic, cellulosic, polysaccharides, polyethylene glycols, polyvinyl-pyrrolidones, alginates and similar substances are suitable for this purpose. This support can also be solid, liquid or pastry. Products which allow the culture to be carried by a spongy layer are very suitable, for example polyvinyl-pyrrolidone foam or its copolymers with vinyl acetate, spongy cellulose or even a gelatin sponge. It is particularly practical to provide the composition according to the invention in the form of a flexible sheet, for example with a support of gelatin, collagen, polyethylene glycol, dextrane or other film-forming compound of this type. This cellular layer is inserted between two other inert protective layers, one of which can be removed at the time of application to the skin of the user. In other cases, upon application, the first protective layer is removed, the cellular layer and the second protective layer are applied, then this 2nd layer is removed, so that the cellular layer becomes integrated with the skin, in particular when the support is a collagen film. Thus, an article is provided in the form of a sheet, the dimensions and shape of which are adapted to the region of the body where application is to take place.

In another embodiment, the above-mentioned support is placed in a very shallow receptacle serving as a protector for the assembly and, if required, allowing use of a liquid or pasty support.

The various forms of the invention are described in more detail below, with reference to the accompanying drawing.

Figure 1:
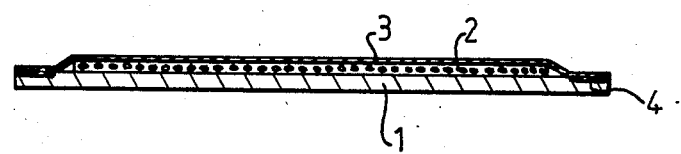
FIG. 1 shows a transverse section of a sheet according to the invention having three superposed layers.

In FIG. 1, the cross-section of an assembly is shown, formed by a flat support 1 carrying cells 2, particularly fibroblasts, with their nutrient culture medium incorporated; this active layer is itself covered with a protective film 3, capable of being removed from 1 at the time of use of the triple sheet 1,2,3. The films 3 and 1 are impermeable to the cell culture medium utilised.

It is important to choose for 1 and 3 suitable materials for cultures of the cells employed without risking alteration of the latter.

As the support 1 comes into contact with the skin, on application of the article, it is desirable that at least its superficial layer carries or contains a sufficiently high number of fibroblasts, preferably $10^4$ to $10^8$ cells per ml.

The active layer represented by 2 in the drawings comprises cells, preferably fibroblastic, but which can if desired be or contain keratinocytes, lymphocytes etc., dispersed in the culture medium utilised. The active layer 2 is shown as a distinct layer, but when the support 1 is sufficiently absorbent of the culture, this can be located partly or wholly in the layer formed by the support 1.

In a particular embodiment, the culture 2 is entirely mixed with the material of the support. This is the case with collagen or a gelling product, for example polyvinyl-pyrrolidone, gelatin or a polysaccharide, dispersed in the liquid medium containing the multiplied cells. In this case, the two protective films are identical or similar.

Preferably, the periphery of the layer 1 is provided with an adhesive to allow attachment of the sheet 1,2 to the skin of the patient after removal of the protective film 3. As it is known to use adhesive tapes suitable for the human skin, particularly in dressings, for example in the form of sticking plaster, it is not necessary to describe here the nature of these adhesive edges 4 (FIG. 1) attached to the articles according to the invention.

As regards the layer 3 covering the culture, as it is not for contact with the skin being treated, it is constituted by a thin film of flexible material, preferably a polymer insoluble in water and inert to the culture medium. Particularly suitable are films of polyethylene, polypropylene, polyamide, polyacrylates, cellulose acetate, cellulose or the like.

While the thicknesses and other dimensions of the articles of sheet form according to the invention can vary widely, advantageously use is made of products where the support 1 has a thickness of about 0.05 to 1 mm, the active layer 2 is 0.1 to 3 mm and the protective film 3 is 0.05 to 0.5 mm. The other preferred dimensions are of the order of 2×5 to 7×15 cm for the width x length and more particularly 4×7 cm, permitting easy application to the face, the hands or the legs. These sheets are polygonal, having rounded edges and, in particular, a trapezoidal form allowing coverage of a major part of the cheek.

Figure 2:
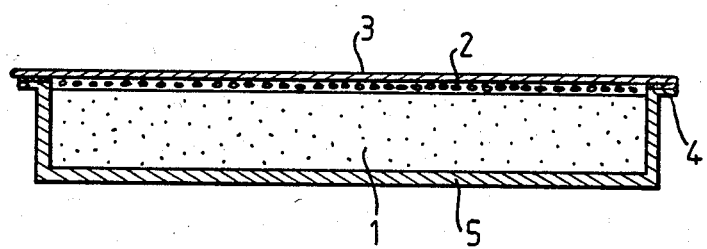
FIG. 2 is also a transverse section of an article according to the invention, where the support for the cells is located in a receptacle of very small depth.
Figure 3:
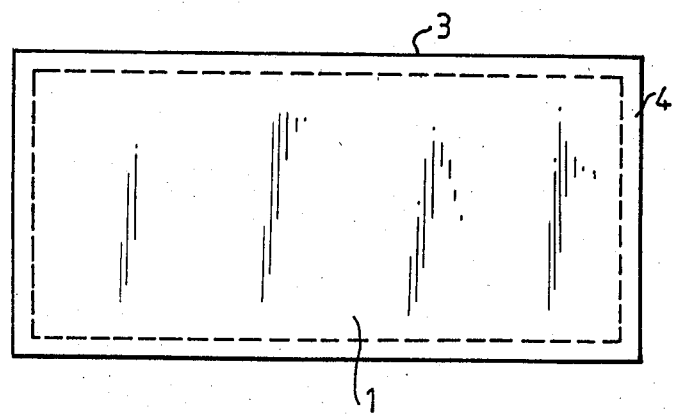
FIG. 3 is a plan view of the article according to FIG. 2.

The device according to FIGS. 2 and 3 comprises the same layers 1 to 3 as that of FIG. 1, but in general the support 1 is thicker and can be particulate and/or liquid. This support is located in a receptacle 5 of depth, for example, 3 to 15 mm and preferably 5 to 10 mm. The periphery 4 is coated with adhesive, allowing temporary fixing on the skin of the receptacle 5 with its support 1 carrying the cells 2, when the protective film 3 has been removed. On use of the product, the composition 1,2 can be taken from the receptacle 5, for example by means of a compress; if necessary, the compress absorbs the excess of the liquid phase present and, loaded with the cells 2, is applied to the skin, thus giving contact of the cells 2 with the latter.

Another article according to the invention comprising the new composition includes a receptacle, for example a rigid or flexible tube provided with an applicator and filled with the composition. This can in particular be a syringe of appropriate capacity. Preferably, such an article comprises a measuring tube avoiding multiple uses, capable of causing pollution as is always possible, particularly with nutrient media and cells.

According to a variant of the invention, the support 1 can comprise microspheres, for example of glass or insoluble polysaccharide ('Sephadex') dispersed in the nutrient culture medium. This gives better transfer of the active elements, on application of the composition to the skin. As cellular development, during culture, takes place on the microparticles, the nutrient liquid can be separated, which in practice leaves a paste for application to the skin.

In the case of this variant of the invention, the preferred mode of preparation of the cosmetic composition consists in first dispersing the particles in the selected nutrient liquid, then seeding this with the cells, particularly fibroblasts and allowing the cells to multiply. Conditioning of the culture thus obtained can be carried out, in the cold, according to one of the methods described above, the assembly being stored with an excess of liquid. It is recommend however to separate the liquid from the microspheres before their application to the skin of a subject.

In addition to the forms described, the new composition can also be employed in the form of a paste or pomade. A thickener is dispersed in the completed and chilled culture, which can for example be one of those cited above in the description of the support 1.

We claim:

1. Cosmetic composition for treatment of the skin, comprising a medium for the culture of cells, characterised in that it comprises effective amounts of living cells of conjunctive tissue in a nutrient medium in which growth of the cells can take place.

2. Composition according to claim 1, characterised in that the major part of the cells are derived from their culture in the medium.

3. Composition according to claim 1 or 2, characterised in that it contains $10^2$ to $10^8$ cells per ml.

4. Composition according to claim 1 characterised in that it is associated with a flat support having an adhesive-coated periphery and covered with a film which is insoluble in water.

5. Composition according to claim 4, characterised in that the support is a collagenic material, a polysaccharide, polyvinyl-pyrrolidone, polyethylene glycol, cellulose, cellulose acetate or a copolymer of polyvinyl-pyrrolidone/vinyl acetate.

6. Composition according to claim 4 or 5, characterised in that the support is in a spongy form.

7. Composition according to claim 1 characterised in that the nutrient medium for the culture is modified Eagle medium together with foetal calf serum, glutamine, sodium pyruvate and amino acids.

8. Composition according to claim 4 characterised in that the support is placed in a receptacle of shallow depth.

9. Composition according to claim 1 characterised in that microparticles are dispersed in the nutrient medium.

10. Composition according to claim 1 characterised in that it is in the form of a paste or a pomade, the liquid nutrient medium including a thickener.

11. Process of preparation of the composition according to claim 1 which comprises effecting culture of the cells of a conjunctive tissue in a nutrient medium and then the culture obtained is fixed to a gel-forming or spongy absorbent support.

12. Process according to claim 11, characterised in that culture of the cells is effected in a modified Eagle nutrient medium, glutamine, sodium pyruvate and amino acids, at 37° C.

13. Process of preparation of the composition according to claim 1, by the culture of fibroblasts in a nutrient medium, characterised in that microparticles are dispersed in the medium before seeding with cells obtained from the skin and that the liquid is separated from the microparticles which serve as the support for the composition.

14. A composition according to claim 1 in which said cells are fibroblasts.

15. Composition according to claim 3 characterized in that it contains $10^4$ to $10^8$ cells per ml.

16. Composition according to claim 9 characterized in that the microparticles are microspheres of glass or insoluble polysaccharides.

17. Process according to claim 11 characterized in that the cells are fibroblasts.

18. Process according to claim 13 characterized in that the microparticles are glass or insoluble polysaccharides.

* * * * *